United States Patent
Azar (10) Patent No.: US 8,216,309 B2
(45) Date of Patent: *Jul. 10, 2012

(54) VISION PROSTHESIS

(75) Inventor: Dimitri Azar, Brookline, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 901 days.

This patent is subject to a terminal disclaimer.

(21) Appl. No.: 11/415,688

(22) Filed: May 1, 2006

(65) Prior Publication Data

US 2006/0206205 A1    Sep. 14, 2006

Related U.S. Application Data

(63) Continuation of application No. 10/627,943, filed on Jul. 25, 2003, now Pat. No. 7,041,133, which is a continuation of application No. 09/909,933, filed on Jul. 20, 2001, now Pat. No. 6,638,304.

(51) Int. Cl.
*A61F 2/16* (2006.01)

(52) U.S. Cl. .............. 623/6.37; 623/6.13; 623/6.22
(58) Field of Classification Search ............... 623/6.11, 623/6.22, 6.24, 6.27, 6.37
See application file for complete search history.

(56) References Cited

U.S. PATENT DOCUMENTS

| | | | |
|---|---|---|---|
| 4,190,330 | A | 2/1980 | Berreman |
| 4,230,942 | A | 10/1980 | Stauffer |
| 4,309,603 | A | 1/1982 | Stauffer |
| 4,373,218 | A | 2/1983 | Schachar |
| 4,466,703 | A | 8/1984 | Nishimoto |
| 4,601,545 | A | 7/1986 | Kern |
| 4,787,903 | A | 11/1988 | Grendahl |
| 5,066,301 | A | 11/1991 | Wiley |
| 5,182,585 | A | 1/1993 | Stoner |
| 5,359,444 | A | 10/1994 | Piosenka et al. |
| 5,593,437 | A | 1/1997 | Arita et al. |
| 5,793,704 | A | 8/1998 | Freger |
| 5,800,530 | A | 9/1998 | Rizzo, III |

*Primary Examiner* — William H. Matthews
(74) *Attorney, Agent, or Firm* — Fish & Richardson P.C.

(57) ABSTRACT

A vision prosthesis includes an intra-ocular lens system having a variable focal length; and a controller that causes a change in the focal length thereof.

20 Claims, 10 Drawing Sheets

VISION PROSTHESIS

RELATED APPLICATIONS

This application is a continuation of U.S. application Ser. No. 10/627,943, filed Jul. 25, 2003, and which issued as U.S. Pat. No. 7,041,133 on May 9, 2006 which is a continuation application of U.S. application Ser. No. 09/909,933, which was filed Jul. 20, 2001 and which issued as U.S. Pat. No. 6,638,304 on Oct. 28, 2003. The contents of the foregoing applications are incorporated herein in their entirety by reference.

FIELD OF INVENTION

This invention relates to a vision prosthesis, and in particular, to prosthetic lenses.

BACKGROUND

In the course of daily life, one typically regards objects located at different distances from the eye. To selectively focus on such objects, the focal length of the eye's lens must change. In a healthy eye, this is achieved through the contraction of a ciliary muscle that is mechanically coupled to the lens. To the extent that the ciliary muscle contracts, it deforms the lens. This deformation changes the focal length of the lens. By selectively deforming the lens in this manner, it becomes possible to focus on objects that are at different distances from the eye. This process of selectively focusing on objects at different distances is referred to as "accommodation".

As a person ages, the lens loses plasticity. As a result, it becomes increasingly difficult to deform the lens sufficiently to focus on objects at different distances. To compensate for this loss of function, it is necessary to provide different optical corrections for focusing on objects at different distances.

One approach to applying different optical corrections is to carry different pairs of glasses and to swap glasses as the need arises. For example, one might carry reading glasses for reading and a separate pair of distance glasses for driving. This is inconvenient both because of the need to carry more than one pair of glasses and because of the need to swap glasses frequently.

Bifocal lenses assist accommodation by integrating two different optical corrections onto the same lens. The lower part of the lens is ground to provide a correction suitable for reading or other close-up work while the remainder of the lens is ground to provide a correction for distance vision. To regard an object, a wearer of a bifocal lens need only maneuver the head so that rays extending between the object-of-regard and the pupil pass through that portion of the bifocal lens having an optical correction appropriate for the range to that object.

The concept of a bifocal lens, in which different optical corrections are integrated into the same lens, has been generalized to include trifocal lenses, in which three different optical corrections are integrated into the same lens, and continuous gradient lenses in which a continuum of optical corrections are integrated into the same lens. However, just as in the case of bifocal lenses, optical correction for different ranges of distance using these multifocal lenses relies extensively on relative motion between the pupil and the lens.

Once a lens is implanted in the eye, the lens and the pupil move together as a unit. Thus, no matter how the patient's head is tilted, rays extending between the object-of-regard and the pupil cannot be made to pass through a selected portion of the implanted lens. As a result, multifocal lenses are generally unsuitable for intraocular implantation because once the lens is implanted into the eye, there can be no longer be relative motion between the lens and the pupil.

A lens suitable for intraocular implantation is therefore generally restricted to being a single focus lens. Such a lens can provide optical correction for only a single range of distances. A patient who has had such a lens implanted into the eye must therefore continue to wear glasses to provide optical corrections for those distances that are not accommodated by the intraocular lens.

SUMMARY

In one aspect, the invention features a vision prosthesis including a variable focal length intra-ocular lens system; and a controller for causing a change in the focal length thereof.

Embodiments of the vision prosthesis include those having a rangefinder for providing the controller with an estimate of a distance to an object-of-regard. Among these embodiments are those having a transducer for detecting a stimulus from an anatomic structure within the eye and providing a signal indicative of the stimulus to the rangefinder.

In one embodiment, the variable lens of the vision prosthesis has an index of refraction that varies in response to a focusing stimulus. An actuator in communication with the lens provides the necessary focusing stimulus on the basis of a range estimate from the rangefinder. A controller coupled to the rangefinder and to the actuator causes the actuator to generate a focusing stimulus on the basis of this range estimate.

Because it is the index of refraction that is changed, the vision prosthesis provides control over the focal length of the lens without the need to mechanically move the lens or any portions thereof. The vision prosthesis thus provides a lens of variable focal length with no moving parts and without the complexity and excessive power consumption associated with a moveable system.

Other embodiments of the vision prosthesis include those having an actuator for receiving a signal from the controller to cause a change in the focal length of the intra-ocular lens system, those having an actuator for changing an index of refraction of the intra-ocular lens system in response to a signal from the controller, and also those having an actuator for mechanically changing the focal length of the intra-ocular lens system in response to a signal from the controller.

In some embodiments, the intra-ocular lens system includes a chamber containing nematic liquid crystal. In others, the intra-ocular lens system includes first and second lens elements; and a motor coupled to the second lens element for moving the second lens element relative to the first lens element.

Additional embodiments further include a manual focusing control for enabling a patient to fine tune focusing of the lens.

In another aspect, the invention features a vision-prosthesis having a variable focal-length intra-ocular lens system; and an actuator coupled to the intra-ocular lens system for causing a change in the focal length thereof.

Some embodiments also include a controller coupled to the actuator for causing the actuator to cause the change in the focal length.

Other embodiments also include a rangefinder for providing an estimate of a distance to an object of regard. This estimate forms a basis for determining an extent to which to vary the focal length.

Yet other embodiments include a transducer for coupling to an anatomic structure within the eye. The transducer generates a signal indicative of a distance to an object-of-regard. This signal provides information to be used in determining an extent to which to vary the focal length.

In another aspect, the invention features a vision prosthesis having a variable focal-length intra-ocular lens system; and a rangefinder for providing an estimate of an extent to which to vary the focal length.

In some embodiments, the rangefinder is configured to provide an estimate at least in part on the basis of activity of an anatomic structure within the eye. Among these embodiments are those that further include a transducer coupled to the anatomic structure and to the rangefinder for providing the rangefinder with information indicative of activity of the anatomic structure.

Other embodiments of the vision prosthesis also include an actuator coupled to the intra-ocular lens system for causing a change to the focal length thereof.

Yet other embodiments of the vision prosthesis further include a controller for receiving information from the rangefinder and causing a change to the focal length of the intra-ocular lens system at least in past on the basis thereof.

These and other features and advantages of the invention will be apparent from the following detailed description and the accompanying figures, in which:

DETAILED DESCRIPTION

Figure 1:
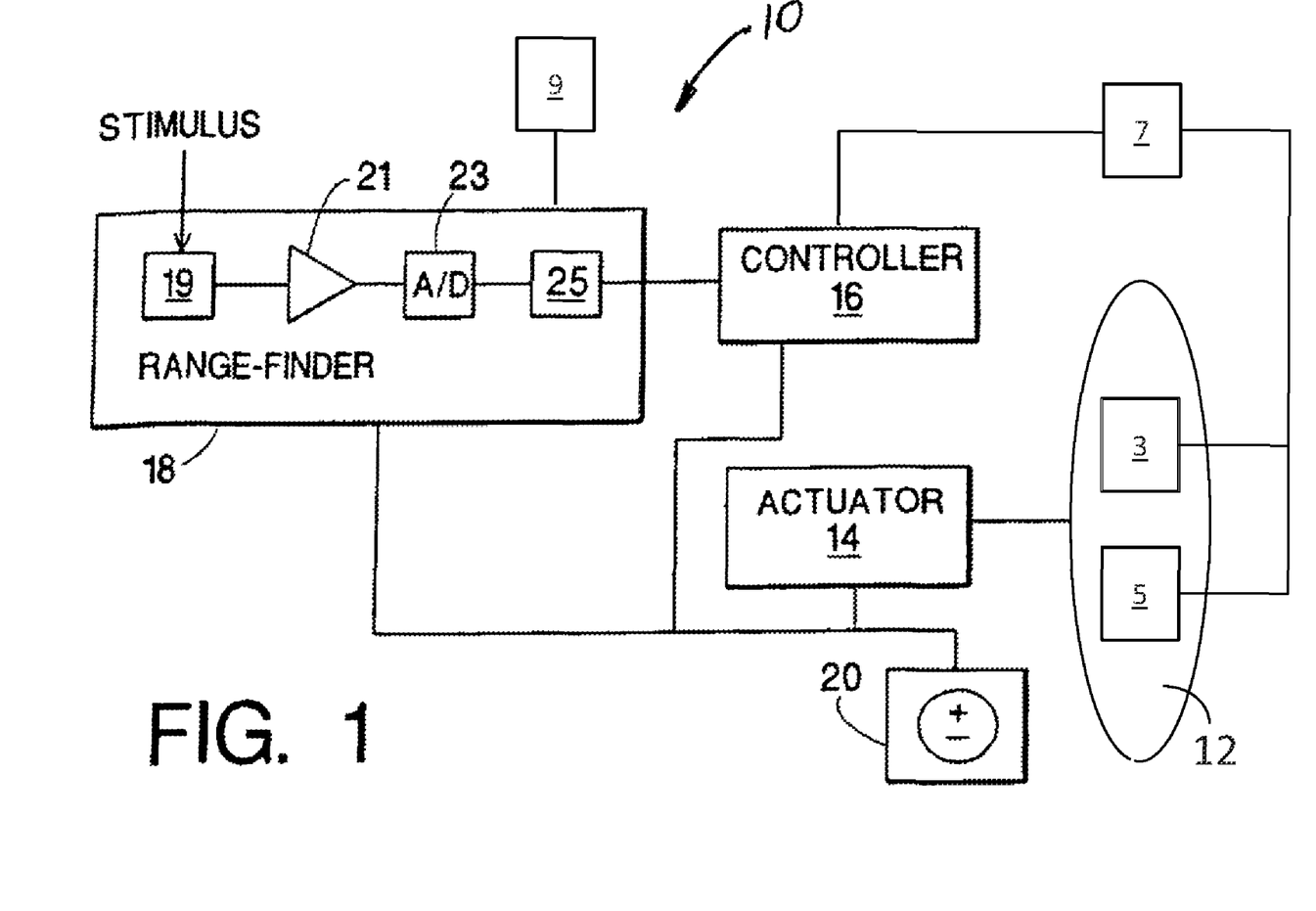
FIG. 1 is a block diagram of the vision prosthesis.

FIG. 1 shows a block diagram of a vision prosthesis 10 having a lens 12 whose index of refraction can be made to vary in response to a focusing signal provided to the lens 12 by an actuator 14. The lens 12 directs light through a nematic liquid-crystal whose index of refraction varies in response to an applied electric field. The actuator 14 includes one or more electrodes in electrical communication with the lens 12. However, the lens 12 can also direct light through a material whose index of refraction varies in response to an applied magnetic field. In this case, the actuator 14 is a magnetic field source, such as a current-carrying coil, in magnetic communication with the lens 12.

Throughout this specification, the terms "lens" and "intraocular lens" refer to the prosthetic lens that is part of the vision prosthesis 10. The lens that is an anatomical structure within the eye is referred to as the "natural lens".

The nature of the focusing signal provided by the actuator 14 controls the extent to which the index of refraction is changed. The actuator 14 generates a focusing signal in response to instructions from a controller 16 in communication with the actuator 14.

The controller 16 is typically a microcontroller having instructions encoded therein. These instructions can be implemented as software or firmware. However, the instructions can also be encoded directly in hardware in, for example, an application-specific integrated circuit. The instructions provided to the microcontroller include instructions for receiving, from a rangefinder 18, data indicative of the distance to an object-of-regard, and instructions for processing that data to obtain a focusing signal. The focusing signal alters the lens' index of refraction to focus an image of the object-of-regard on the retina.

The rangefinder 18 typically includes a transducer 19 for detecting a stimulus from which a range to an object can be inferred. The signal generated by the transducer 19 often requires amplification before it is of sufficient power to provide to the controller 16. Additionally, the signal may require some preliminary signal conditioning. Accordingly, in addition to a transducer 19, the rangefinder 18 includes an amplifier 21 to amplify the signal, an A/D converter 23 to sample the resultant amplified signal, and a digital signal processor 25 to receive the sampled signal. The output of the digital signal processor 25 is provided to the controller 16.

A power source 20 supplies power to the controller 16, the range finder 18, and the actuator 14. A single power source 20 can provide power to all three components. However, the vision prosthesis 10 can also include a separate power source 20 for any combination of those components that require power.

1. Intraocular Vision Prosthesis
1.1 Lens and Actuator

Figure 2:
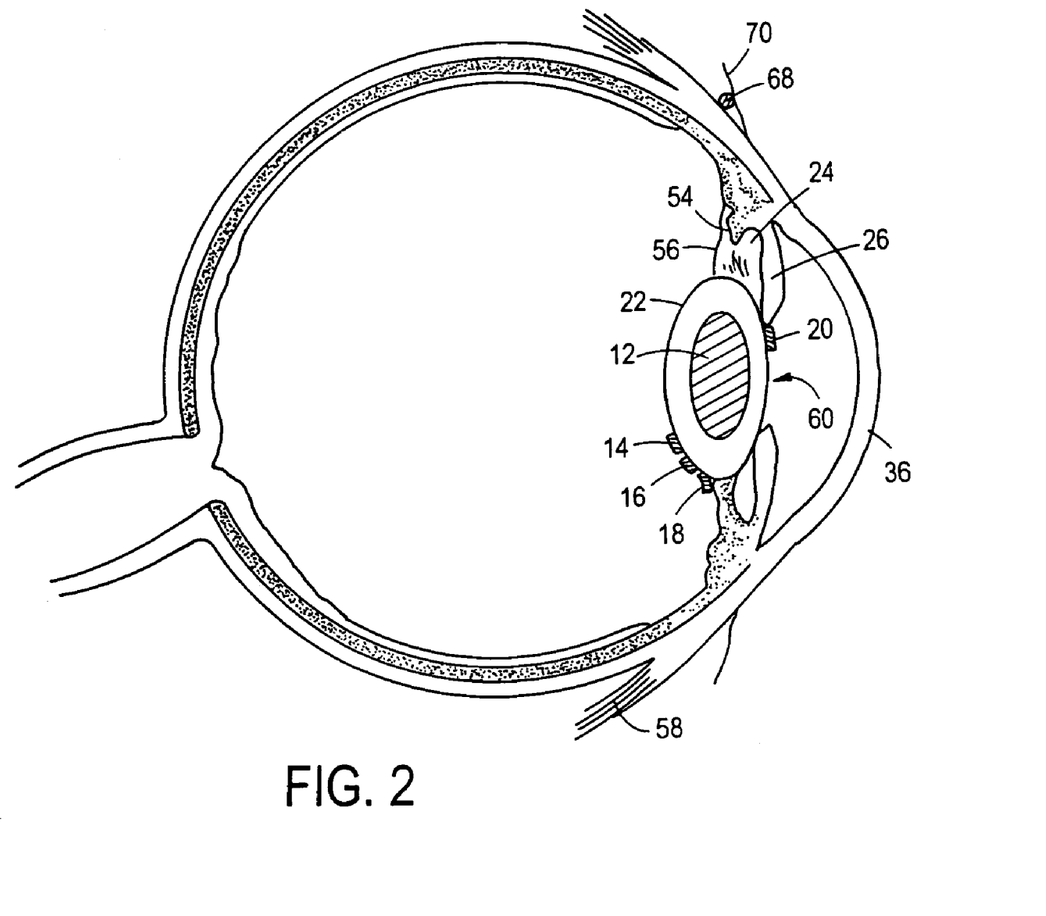
FIGS. 2-5 show the vision prosthesis of FIG. 1 implanted at various locations within the eye.
Figure 3:
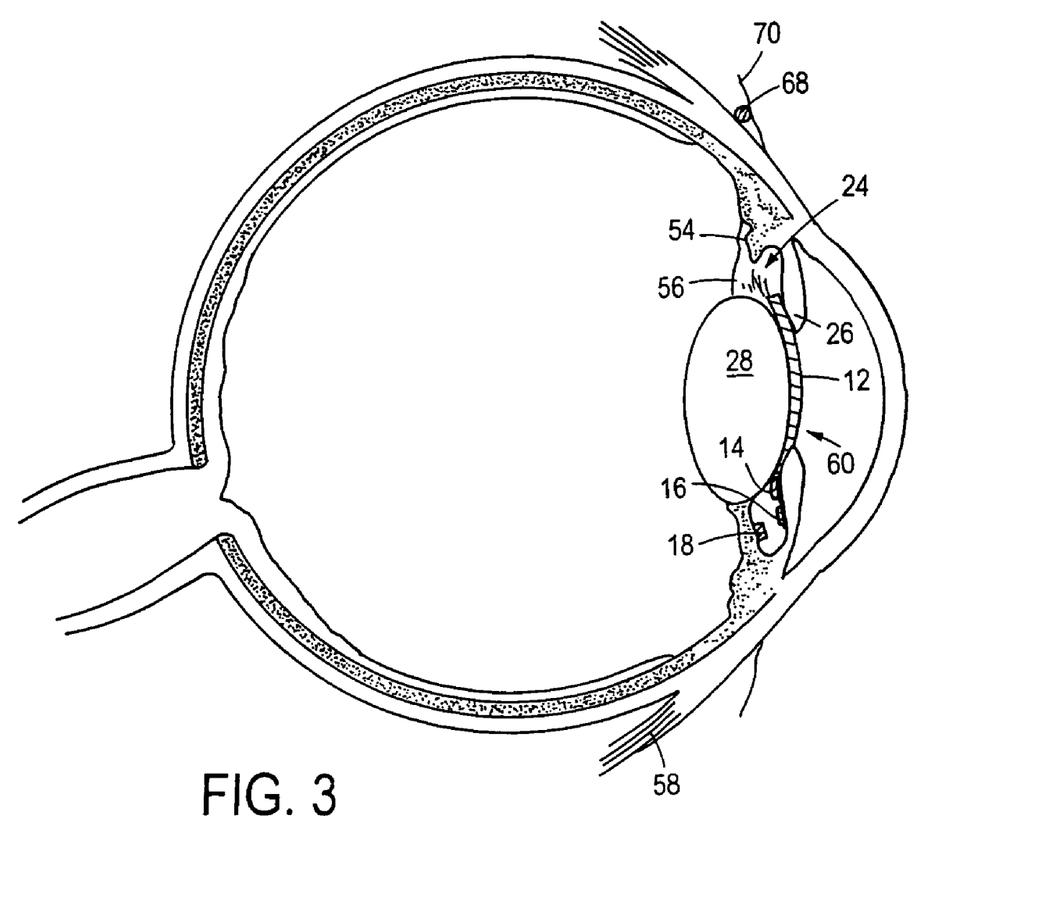
Figure 4:
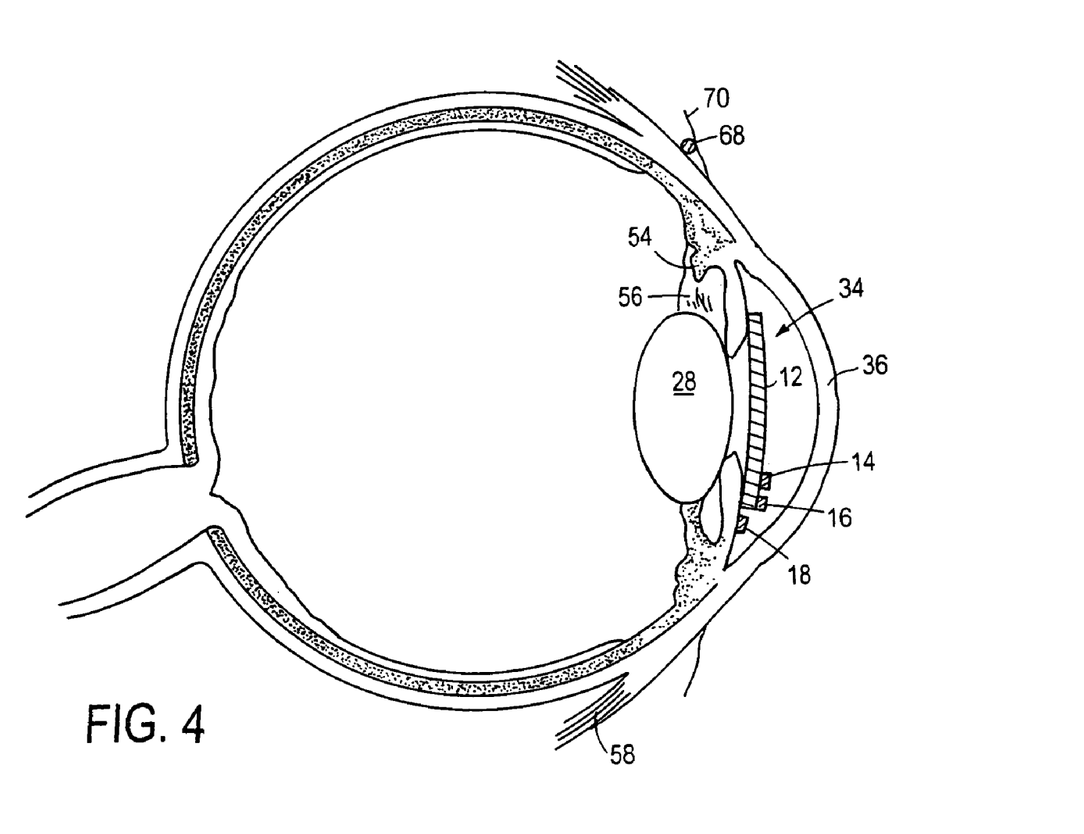
Figure 5:
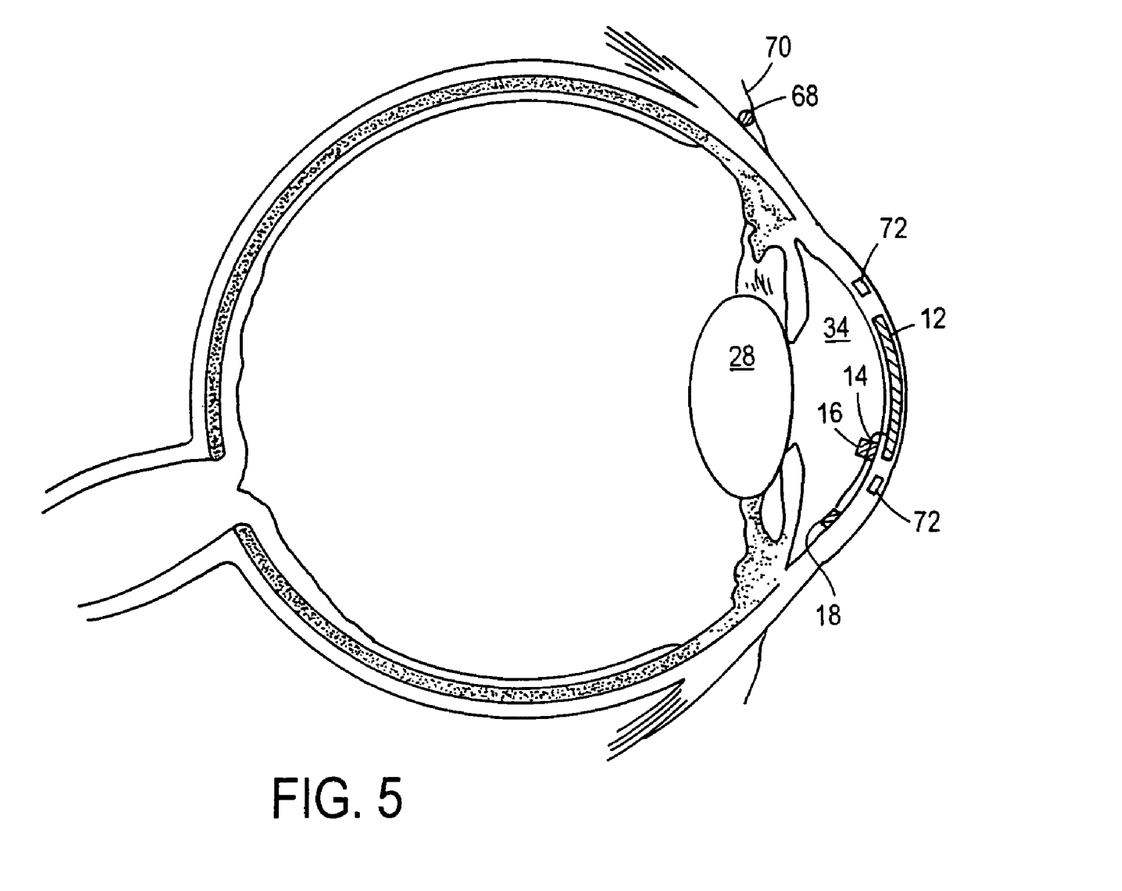

In one embodiment of the vision prosthesis 10, the lens 12 is an intraocular lens. The intraocular lens 12 can be implanted into an aphakic patient, as shown in FIG. 2, in which case it can be implanted into the lens-bag 22 from which the patient's natural lens has been removed. Alternatively, the intraocular lens 12 can be implanted into a phakic patient, in which case it can be implanted into the posterior chamber 24, between the iris 26 and the patient's natural lens 28, as shown in FIG. 3. With the intraocular lens 12 implanted in the posterior chamber 24, the haptic 30 of the lens 12 rests in the sulcus 32. The intraocular lens 12 can also be implanted in the anterior chamber 34, as shown in FIG. 4, or in the cornea 36, as shown in FIG. 5.

Preferably, the lens 12 is a foldable lens having a tendency to spring back to its unfolded position. Such a lens 12 can be inserted through a small incision, maneuvered into the desired location, and released. Once released, the lens 12 springs back to its unfolded position.

Figure 6:
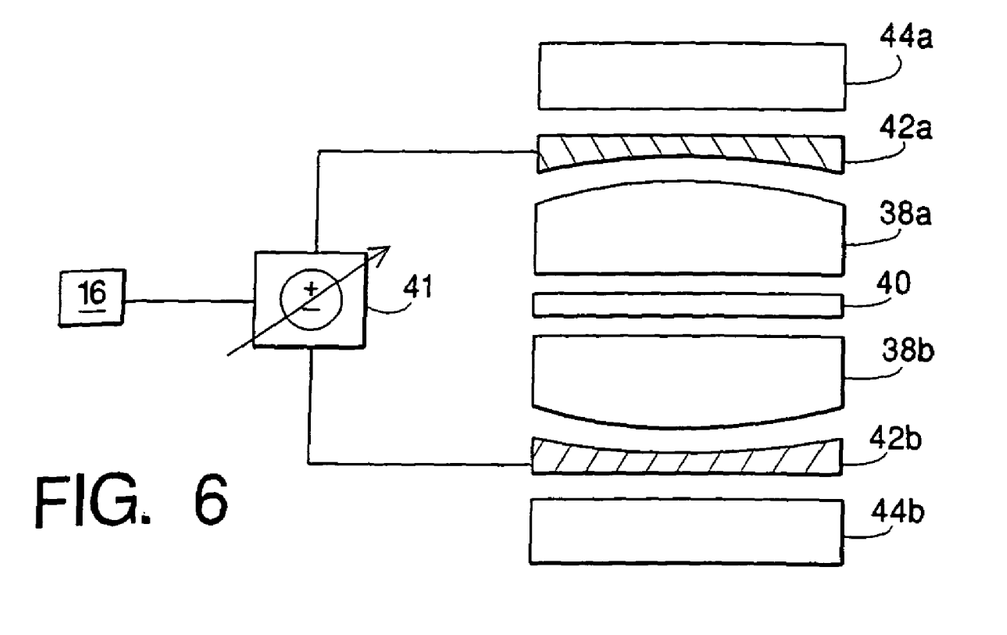
FIGS. 6, 7A, and 7B show two embodiments of the lens and actuator of FIG. 1.

In one embodiment of the lens 12, shown in exploded view in FIG. 6, first and second curved chambers 38a, 38b filled with nematic liquid-crystal are separated by a transparent plate 40. In this embodiment, the actuator 14 includes a variable voltage source 41 connected to two transparent electrodes 42a, 42b disposed on an outer surface of each curved chamber 38a, 38b. The variable voltage source 41 generates a variable voltage in response to instructions from the controller 16. First and second transparent outer layers 44a, 44b cover the first and second electrodes 42a, 42b respectively.

When the variable voltage source 41 applies a voltage, the first and second electrodes 42a, 42b impose an electric field in the nematic liquid-crystal. This electric field tends to reorient the directors of the nematic liquid-crystal, thereby changing its index of refraction. A lens assembly of this type is described fully in U.S. Pat. No. 4,190,330, the contents of which are herein incorporated by reference.

Figure 7A:
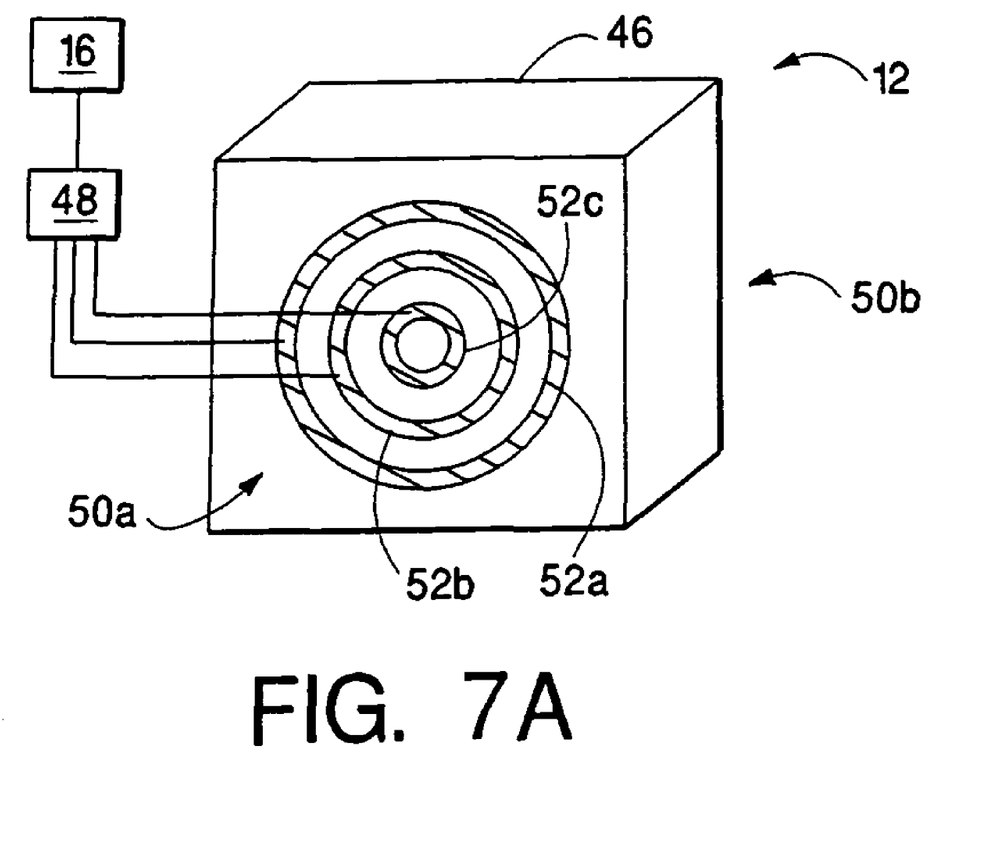

In another embodiment, shown in FIG. 7A, the lens 12 includes a thin chamber 46 filled with nematic liquid-crystal and the actuator 14 includes a variable voltage source 48 and first and second sets 50a, 50b of electrodes 52a-c disposed on opposed planar surfaces of the thin chamber 46. Each of the electrodes 52a-c is individually addressable by the controller 16. A voltage maintained across a electrode 52a form the first set 50a and a corresponding electrode from the second set 50b results in an electric field across a local zone of the nematic liquid-crystal adjacent to those electrodes. This electric field reorients the directors, and hence alters the index of refraction, within that zone. As a result, the index of refraction can be made to vary at different points of the lens 12.

Figure 7B:
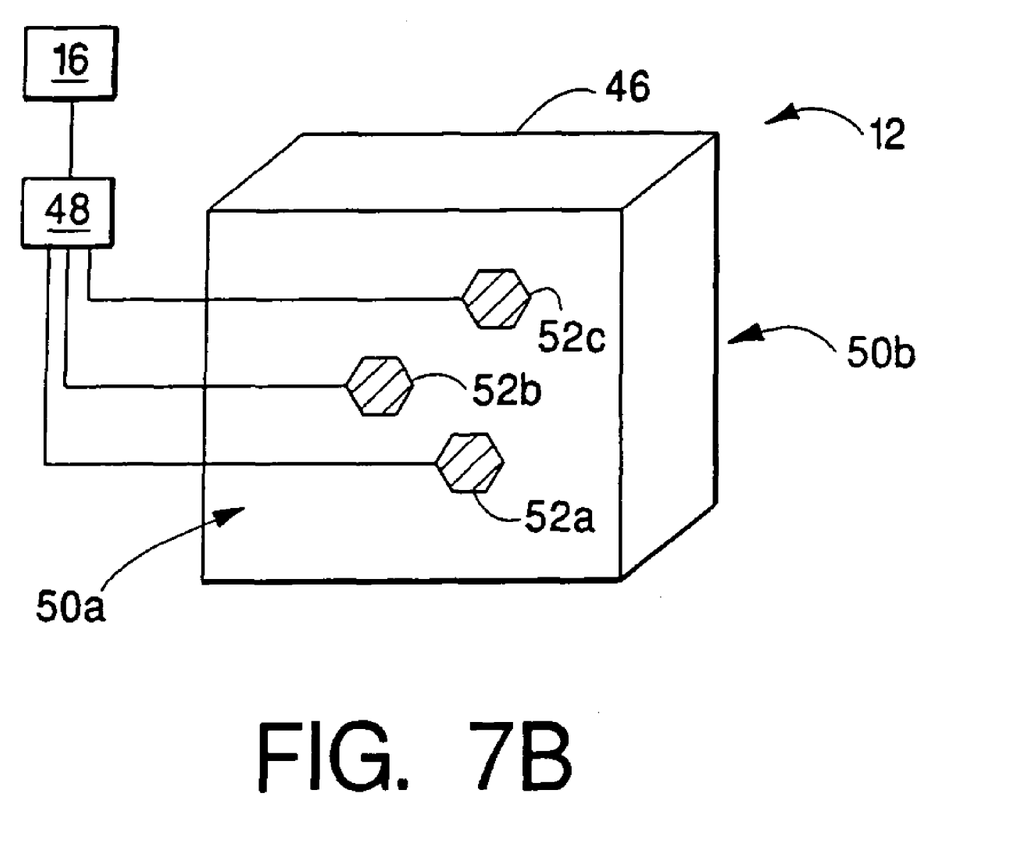

FIG. 7A shows a lens assembly having concentric electrodes 52a-c. A lens assembly of this type is described fully in U.S. Pat. No. 4,466,703, the contents of which are herein incorporated by reference. In this embodiment, the index of refraction can be altered as a function of distance from the center of the lens 12. However, individually addressable electrodes 52a-c can also be arranged in a two-dimensional array on the surface of the lens 12. When this is the case, the index of refraction can be varied as a function of two spatial variables. The grid of electrodes 52a-c can be a polar grid, as shown in FIG. 7A, or a rectilinear grid, as shown in FIG. 7B. The electrodes 52a-c can be distributed uniformly on the grid, or they can be distributed more sparsely in certain regions of the lens 12 and more densely in other regions of the lens 12.

Because of its thin planar structure, a lens 12 of the type shown in FIG. 6 is particularly suitable for implantation in constricted spaces, such as in the posterior chamber 24 of a phakic patient, as shown in FIG. 3.

In another embodiment, the lens 12 includes a chamber filled with a nematic liquid-crystal and the actuator 14 is a current-carrying coil that generates a magnetic field. In this embodiment, the controller 16 causes current to flow in the coil. This current supports a magnetic field that reorients the directors in the nematic liquid-crystal. This results in a change in the liquid crystal's index of refraction.

The extent to which the index of refraction of a nematic liquid crystal can be changed is limited. Once all the directors in the nematic liquid crystal have been polarized, increasing the magnitude of the imposed electric field has no further effect. A nematic liquid crystal in this state is said to be saturated. To change the focal length beyond the point at which the nematic crystal is saturated, a lens 12 can also include one or more lens elements 3 and 5 that are moved relative to each other by actuators embodied, e.g., as micromechanical motors 7.

Alternatively, the lens can have a baseline curvature that and also be filled with nematic crystal. The baseline curvature can be used to perform a gross correction that can be fine-tuned by locally varying the index of refraction of the lens material.

In another embodiment, the lens is made up of a multiplicity of lenslets, as shown in FIG. 7B, each of which has its own baseline curvature and each of which is filled with nematic crystal. An individually addressable electrode is then connected to each of the lenslets. In this embodiment, both the lens curvature and the index of refraction can be varied locally and can be varied as a function of two spatial variables.

1.2 Rangefinder

In a normal eye, contraction of a ciliary muscle 54 is transmitted to the natural lens 28 by zonules 56 extending between the ciliary muscle 54 and the lens-bag 22. When the object-of-regard is nearby, the ciliary muscle 54 contracts, thereby deforming the natural lens 28 so as to bring an image of the object into focus on the retina. When the object-of-regard is distant, the ciliary muscle 54 relaxes, thereby restoring the natural lens 28 to a shape that brings distant objects into focus on the retina. The activity of the ciliary muscle 54 thus provides an indication of the range to an object-of-regard.

For an intraocular lens 12, the transducer 19 of the rangefinder 18 can be a transducer for detecting contraction of the ciliary muscle 54. In one embodiment, the rangefinder 18 can include a pressure transducer that detects the mechanical activity of the ciliary muscle 54. A pressure transducer coupled to the ciliary muscle 54 can be a piezoelectric device that deforms, and hence generates a voltage, in response to contraction of the ciliary muscle 54. In another embodiment, the transducer can include an electromyograph for detecting electrical activity within the ciliary muscle 54.

As noted above, the activity of the ciliary muscle 54 is transmitted to the natural lens 28 by zonules 56 extending between the ciliary muscle 54 and the lens-bag 22. Both the tension in the zonules 56 and the resulting mechanical disturbance of the lens-bag 22 can be also be used as indicators of the distance to the object-of-regard. In recognition of this, the rangefinder 18 can also include a tension measuring transducer in communication with the zonules 56 or a motion sensing transducer in communication with the lens-bag 22. These sensors can likewise be piezoelectric devices that generate a voltage in response to mechanical stimuli.

The activity of the rectus muscles 58 can also be used to infer the distance to an object-of-regard. For example, a contraction of the rectus muscles 58 that would cause the eye to converge medially can suggest that the object-of-regard is nearby, whereas contraction of the rectus muscles 58 that would cause the eye to gaze forward might suggest that the object-of-regard is distant. The rangefinder 18 can thus include a transducer that responds to either mechanical motion of the rectus muscles 58 or to the electrical activity that triggers that mechanical motion.

It is also known that when a person intends to focus on a nearby object, the iris 26 contracts the pupil 60. Another embodiment of the rangefinder 18 relies on this contraction to provide information indicative of the distance to the object-of-regard. In this embodiment, the rangefinder 18 includes a transducer, similar to that described above in connection with the rangefinder 18 that uses ciliary muscle or rectus muscle activity, to estimate the distance to the object-of-regard. Additionally, since contraction of the pupil 60 diminishes the light incident on the lens 12, the transducer 19 of the rangefinder 18 can include a photodetector for detecting this change in the light.

The foregoing embodiments of the rangefinder 18 are intended to be implanted into a patient, where they can be coupled to the anatomical structures of the eye. This configuration, in which the dynamic properties of one or more anatomical structures of the eye are used to infer the distance to an object-of-regard, is advantageous because those properties are under the patient's control. As a result, the patient can, to a certain extent, provide feedback to the rangefinder 18 by controlling those dynamic properties. For example, where the rangefinder 18 includes a transducer responsive to the ciliary muscle 54, the patient can control the index of refraction of the intraocular lens 12 by appropriately contracting or relaxing the ciliary muscle 54.

Other embodiments of the rangefinder 18 can provide an estimate of the range without relying on stimuli from anatomic structures of the eye. For example, a rangefinder 18 similar to that used in an auto-focus camera can be implanted. An example of such a rangefinder 18 is one that transmits a beam of infrared radiation, detects a reflected beam, and estimates range on the basis of that reflected beam. The output of the rangefinder 18 can then be communicated to the actuator 14. Since a rangefinder 18 of this type does not rely on stimuli from anatomic structures of the eye, it need not be implanted in the eye at all. Instead, it can be worn on an eyeglass frame or even hand-held and pointed at objects of regard. In such a case, the signal from the rangefinder 18 can be communicated to the actuator 14 either by a wire connected to an implanted actuator 14 or by a wireless link.

A rangefinder 18 that does not rely on stimuli from an anatomic structure within the eye no longer enjoys feedback from the patient. As a result, it is desirable to provide a feedback mechanism to enhance the range-finder's ability to achieve and maintain focus on an object-of-regard.

Figure 8:
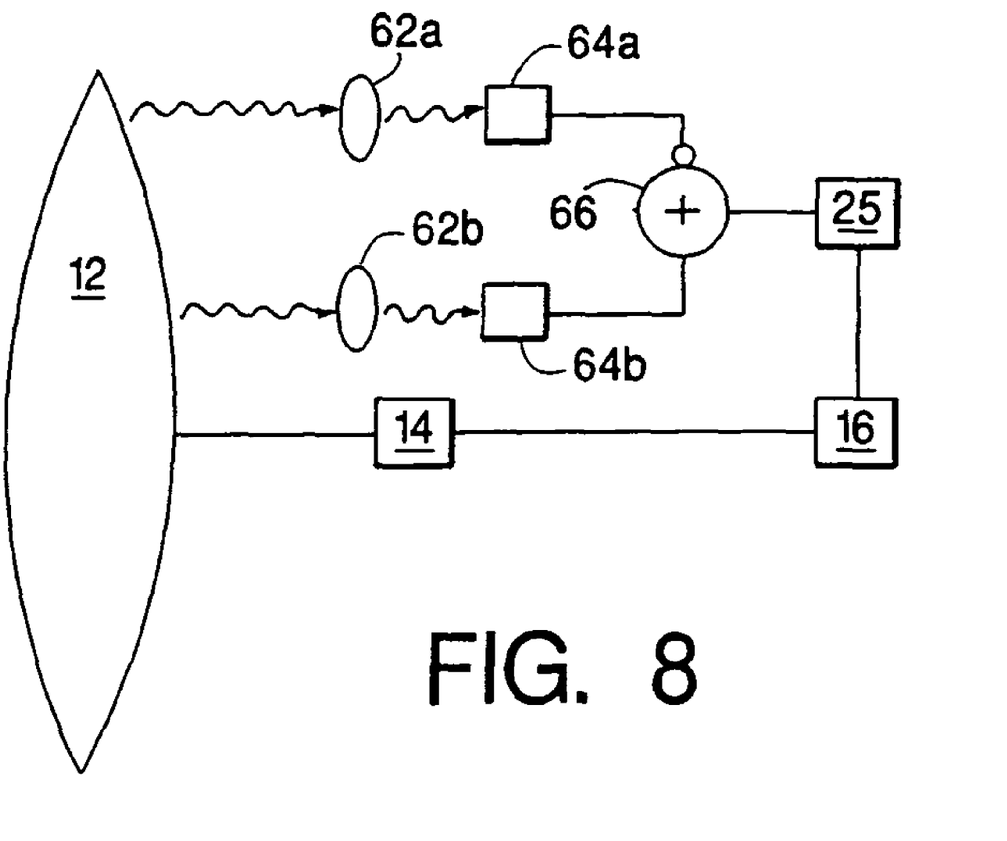
FIG. 8 shows a feedback mechanism for a rangefinder of the vision prosthesis of FIG. 1.

In a feedback mechanism as shown in FIG. 8, first and second lenslets 62a, 62b are disposed posterior to the intraocular lens 12. The first and second lenslets 62a, 62b are preferably disposed near the periphery of the intraocular lens 12 to avoid interfering with the patient's vision. A first photodetector 64a is disposed at a selected distance posterior to the first lenslet 62a, and a second photodetector 64b is disposed at the same selected distance posterior to the second lenslet 62b. The focal length of the first lenslet 62a is slightly greater than the selected distance, whereas the focal length of the second lenslet 62b is slightly less than the selected distance.

The outputs of the first and second photodetectors 64a, 64b are connected to a differencing element 66 that evaluates the difference between their output. This difference is provided to the digital signal processor 25. When the output of the differencing element 66 is zero, the intraocular lens 12 is in focus. When the output of the differencing element 66 is non-zero, the sign of the output identifies whether the focal length of the intraocular lens 12 needs to be increased or decreased, and the magnitude of the output determines the extent to which the focal length of the intraocular lens 12 needs to change to bring the lens 12 into focus. A feedback mechanism of this type is disclosed in U.S. Pat. No. 4,309,603, the contents of which are herein incorporated by reference.

In any of the above embodiments of the rangefinder 18, a manual control 9 can also be provided to enable a patient to fine-tune the focusing signal. The digital signal processor 25 can then use any correction provided by the user to calibrate the range estimates provided by the rangefinder 18 so that the next time that that range estimate is received, the focusing signal provided by the digital signal processor 25 will no longer need fine-tuning by the patient. This results in a self-calibrating vision prosthesis 10.

The choice of which of the above range-finders is to be used depends on the particular application. For example, a lens 12 implanted in the posterior chamber 24 has ready access to the ciliary muscle 54 near the haptic 30 of the lens 12. Under these circumstances, a rangefinder that detects ciliary muscle activity is a suitable choice. A lens 12 implanted in the anterior chamber 34 is conveniently located relative to the iris 26 but cannot easily be coupled to the ciliary muscle 54. Hence, under these circumstances, a rangefinder that detects contraction of the iris 26 is a suitable choice. A lens 12 implanted in the cornea 36 is conveniently located relative to the rectus muscles 58. Hence, under these circumstances, a rangefinder that detects contraction of the rectus muscles 58 is a suitable choice. In the case of an aphakic patient, in which the natural lens 28 in the lens-bag 22 has been replaced by an intraocular lens 12, a rangefinder that detects zonule tension or mechanical disturbances of the lens-bag 22 is a suitable choice. In patients having a loss of function in any of the foregoing anatomical structures, a rangefinder that incorporates an automatic focusing system similar to that used in an autofocus camera is a suitable choice.

1.3 Power Source

As noted above, the controller 16, the rangefinder 18, and the actuator 14 shown in FIG. 1 require a power source 20. In one embodiment, the power source 20 can be an implanted battery 68. The battery 68 can be implanted in any convenient location, such as under the conjunctiva 70 in the Therron's capsule, or within the sclera. Unless it is rechargeable in situ, such a power source 20 will periodically require replacement.

In another embodiment, the power source 20 can be a photovoltaic cell 72 implanted in a portion of the eye that receives sufficient light to power the vision prosthesis 10. The photovoltaic cell 72 can be mounted on a peripheral portion of the lens 12 where it will receive adequate light without interfering excessively with vision. Alternatively, the photovoltaic cell 72 can be implanted within the cornea 36, where it will receive considerably more light. When implanted into the cornea 36, the photovoltaic cell 72 can take the form of an annulus or a portion of an annulus centered at the center of the cornea 36. This configuration avoids excessive interference with the patient's vision while providing sufficient area for collection of light.

Power generated by such a photovoltaic cell 72 can also be used to recharge a battery 68, thereby enabling the vision prosthesis 10 to operate under low-light conditions. The use of a photovoltaic cell as a power source 20 eliminates the need for the patient to undergo the invasive procedure of replacing an implanted battery 68.

The choice of a power source 20 depends in part on the relative locations of the components that are to be supplied with power and the ease with which connections can be made to those components. When the lens 12 is implanted in the cornea 36, for example, the associated electronics are likely to be accessible to a photovoltaic cell 72 also implanted in the cornea 36. In addition, a rechargeable subconjunctival battery 68 is also easily accessible to the photovoltaic cell 72. The disposition of one or more photovoltaic cells 72 in an annular region at the periphery of the cornea 36 maximizes the exposure of the photovoltaic cells 72 to ambient light.

When the lens 12 is implanted in the anterior chamber 34, one or more photovoltaic cells 72 are arranged in an annular region on the periphery of the lens 12. This reduces interference with the patient's vision while providing sufficient area for exposure to ambient light. For a lens 12 implanted in the anterior chamber 34, a rechargeable battery 68 implanted beneath the conjunctiva 70 continues to be conveniently located relative to the photovoltaic cells 72.

When the lens 12 is implanted in the posterior chamber 24, one or more photovoltaic cells 72 can be arranged in an annular region of the lens 12. However, in this case, the periphery of the lens 12 is often shaded by the iris 26 as it contracts to narrow the pupil 60. Because of this, photovoltaic cells 72 disposed around the periphery of the lens 12 may receive insufficient light to power the various other components of the vision prosthesis 10. As a result, it becomes preferable to dispose the photovoltaic cells 72 in an annular region having radius small enough to ensure adequate lighting but large enough to avoid excessive interference with the patient's vision.

2. Extraocular Vision Prosthesis

The lens 12 in FIG. 1 need not be an intraocular lens. In an alternative embodiment, shown in FIG. 9, the vision prosthesis 10, including the lens 12, is mounted on a frame 74 and worn in the manner of conventional eyeglasses. This embodiment largely eliminates those constraints on the size and location of the power source 20 that are imposed by the relative inaccessibility of the various anatomical structures of the eye as well as by the limited volume surrounding them.

Figure 9:
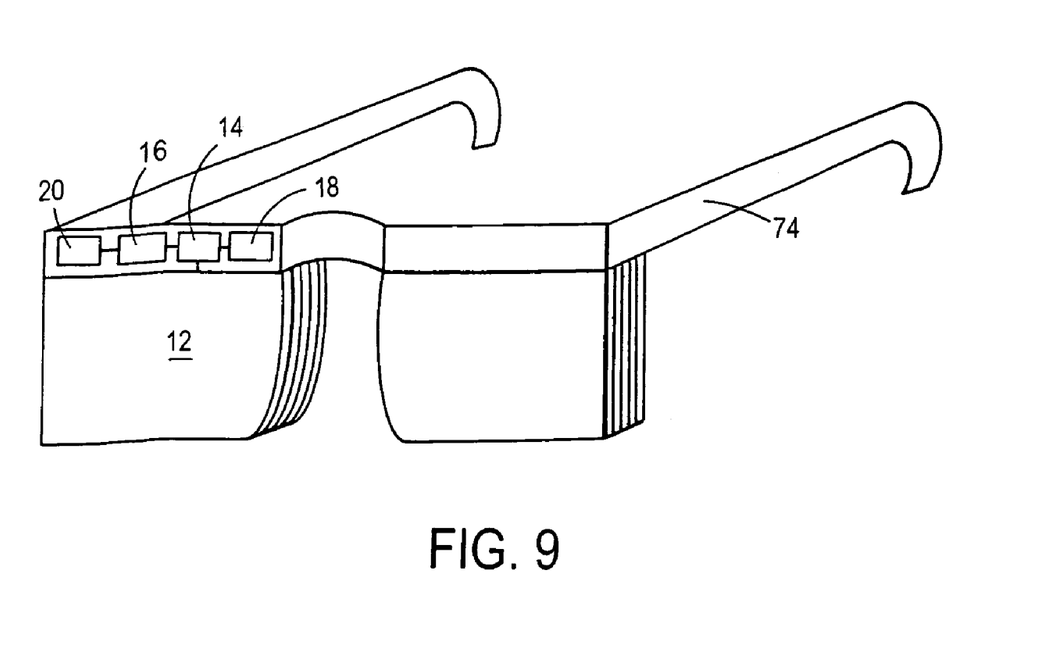
FIG. 9 shows the vision prosthesis of FIG. 1 mounted on an eyeglass frame.

In the embodiment shown in FIG. 9, the rangefinder 18 is typically of the type used in an autofocus camera together with the two-lenslet feedback mechanism described above in connection with the intraocular vision prosthesis 10. The lens 12, its associated actuator 14, and the power source 20 can be selected from any of the types already described above in connection with the intraocular embodiment of the vision prosthesis 10.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Having described the invention, and a preferred embodiment thereof, what I claim as new and secured by Letters Patent is:

1. A vision prosthesis comprising:
    an intra-ocular lens system having a focal length that varies in response to a change in an index of refraction, the intra-ocular lens system comprising a lens element with no moving parts;
    a controller for causing a change in the focal length, the extent of the change being dependent on an estimate of a distance to an object of regard;
    a first actuator for changing an index of refraction of the intra-ocular lens system in response to a signal from the controller; and
    a second actuator for mechanically changing the focal length of the intra-ocular lens system in response to a signal from the controller.

2. The vision prosthesis of claim 1, further comprising a rangefinder for providing the controller with an estimate of a distance to an object-of-regard.

3. The vision prosthesis of claim 1, wherein the intra-ocular lens system comprises a chamber containing nematic liquid crystal.

4. The vision prosthesis of claim 1, wherein the intra-ocular lens system further comprises:
    an additional lens element moveable relative to the lens element with no moving parts; and
    wherein the second actuator comprises a motor coupled to the additional lens element for moving the additional lens element relative to the lens element with no moving parts.

5. The vision prosthesis of claim 2, further comprising a transducer for detecting a stimulus from an anatomic structure within the eye and providing a signal indicative of the stimulus to the rangefinder.

6. The vision prosthesis of claim 4, further comprising a manual focusing control for enabling a patient to fine tune focusing of the lens.

7. The vision prosthesis of claim 1, wherein the second actuator includes a micromechanical motor.

8. A vision-prosthesis comprising:
    an intra-ocular lens system having a focal length that varies in response to a change in an index of refraction, the intra-ocular lens system comprising a lens element with no moving parts and a first actuator for changing an index of refraction of the intra-ocular lens system; and
    a second actuator coupled to the intra-ocular lens system for mechanically causing a change in the focal length thereof, the extent of the change being dependent on an estimate of the distance to an object of regard.

9. The vision prosthesis of claim 8, further comprising a controller coupled to the second actuator for causing the second actuator to cause the change in the focal length.

10. The vision prosthesis of claim 8, further comprising a rangefinder for providing an estimate of a distance to an object of regard, the estimate forming a basis for determining an extent to which to vary the focal length.

11. The vision prosthesis of claim 8, further comprising a transducer for coupling to an anatomic structure within the eye, the transducer generating a signal indicative of a distance to an object-of-regard, the signal providing information to be used in determining an extent to which to vary the focal length.

12. The vision prosthesis of claim 8, wherein the second actuator includes a micromechanical motor.

13. A vision prosthesis comprising:
    an intra-ocular lens system having a focal length that varies in response to a change in an index of refraction, the intra-ocular lens system comprising a lens element with no moving parts;
    a first actuator for changing an index of refraction of the intra-ocular lens system;
    a second actuator coupled to the intra-ocular lens system for mechanically causing a change in the focal length; and
    a rangefinder for providing an estimate of an extent to which to vary the focal length.

14. The vision prosthesis of claim 13, wherein the rangefinder is configured to provide an estimate at least in part on the basis of activity of an anatomic structure within the eye.

15. The vision prosthesis of claim 14, further comprising a transducer configured to be coupled to the anatomic structure and to the rangefinder for providing the rangefinder with information indicative of activity of the anatomic structure.

16. The vision prosthesis of claim 13, further comprising a controller for receiving information from the rangefinder and causing a change to the focal length of the intra-ocular lens system at least in part on the basis of the information.

17. The vision prosthesis of claim 13, wherein the second actuator includes a micromechanical motor.

18. An apparatus comprising:
    an intraocular lens having an index of refraction that varies in response to a focusing stimulus, the intraocular lens comprising a lens element with no moving parts;
    a first actuator in communication with the intraocular lens for providing the focusing stimulus;
    a second actuator coupled to the intra-ocular lens for mechanically causing a change in the focal length;
    a rangefinder for generating a range estimate indicative of a relative distance to an object-of-regard; and
    a controller coupled to the rangefinder and to the actuator for causing the actuator to generate a focusing stimulus on the basis of the range estimate.

19. The apparatus of claim 18, wherein the rangefinder includes a transducer for detecting a stimulus from an anatomic structure in an eye, the stimulus being indicative of a range to the object-of-regard.

20. The apparatus of claim 18, wherein the second actuator includes a micromechanical motor.

* * * * *